United States Patent [19]

Hara et al.

[11] 4,242,430

[45] Dec. 30, 1980

[54] METHOD FOR STABILIZING ORGANIC SUBSTRATE MATERIALS INCLUDING PHOTOGRAPHIC DYE IMAGES AGAINST LIGHT

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 960,548

[22] Filed: Nov. 14, 1978

[30] Foreign Application Priority Data

Nov. 22, 1977 [JP] Japan .................. 52-140321

[51] Int. Cl.$^3$ .................................. G03C 7/00
[52] U.S. Cl. ....................... 430/17; 430/213; 430/220; 430/372; 430/544; 430/551; 430/552; 430/554; 430/556; 430/558; 430/559; 430/561; 260/45.75 R; 260/429 R; 260/438.1; 260/439 R
[58] Field of Search .............. 96/3, 56, 67, 74, 84 R, 96/66.4, 109, 110, 114.5, 119, 99; 252/300 R; 260/429 R, 429 C, 429 J, 438.1, 439 R

[56] References Cited

U.S. PATENT DOCUMENTS

| | | | |
|---|---|---|---|
| 2,352,462 | 6/1944 | Weiss et al. | 260/429 C |
| 2,686,798 | 8/1954 | Gmitter | 260/429 R |
| 3,020,123 | 2/1962 | Schaeffer et al. | 260/429 R |
| 3,082,167 | 3/1963 | Erdman | 260/429 R |
| 3,588,216 | 6/1971 | Bloom | 260/429 R |
| 3,672,898 | 6/1972 | Schwan et al. | 96/74 |
| 3,840,376 | 10/1974 | Shiba et al. | 96/3 |
| 4,050,938 | 9/1977 | Smith, Jr. et al. | 96/84 UV |

OTHER PUBLICATIONS

Complete Electron-Transfer Series of the [m-n$_4$]Type, Balch et al., J.A.C.S., 88:22, Nov. 20, 1966, pp. 5201-5209.

Mech. of Oxid. Photodegradation and of UV Stabiz. of Polyolefins, Cicchetti, Adv. Polymer Sci., vol. 7, pp. 70-112 (1970).

*Primary Examiner*—Travis Brown
*Attorney, Agent, or Firm*—Sughrue, Rothwell, Mion, Zinn and Macpeak

[57] ABSTRACT

Organic substrates, especially photographic dyes, are stabilized against light by using a Cu, Co, Ni, Pd or Pt complex of formula (I).

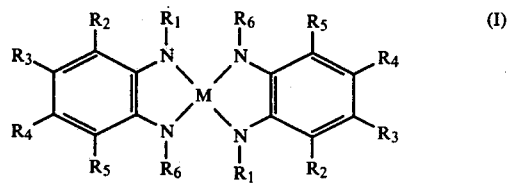

wherein M represents Cu, Co, Ni, Pd or Pt; $R_1$ and $R_6$ may be the same or different and represent a hydrogen atom or an alkyl group, an aryl group, an acyl group, an alkoxycarbonyl group, an aryloxycarbonyl group, an alkylsulfonyl group or an arylsulfonyl group; and $R_2$, $R_3$, $R_4$ and $R_5$ which may be the same or different represent a hydrogen atom, a halogen atom, a cyano group, or an alkyl group, an aryl group, a cycloalkyl group or a heterocyclic group bonded to a carbon atom on a benzene ring directly or through a divalent linking group, or $R_2$ and $R_3$, $R_3$ and $R_4$ or $R_4$ and $R_5$ respectively may combine and represent the non-metallic atomic groupings required to form a 6-membered ring.

14 Claims, No Drawings

METHOD FOR STABILIZING ORGANIC SUBSTRATE MATERIALS INCLUDING PHOTOGRAPHIC DYE IMAGES AGAINST LIGHT

BACKGROUND OF THE INVENTION

1. Field of the Invention

This invention relates to a method for stabilizing organic substrates against light, and more specifically, to a method for stabilizing organic compounds, especially organic dyes, against light.

2. State of the Art

It is generally known that organic substrates, for example organic dyes, tend to fade in color or discolor when subjected to the action of light. Investigations have been made in the fields of inks, textile dyeing, color photography, etc. to prevent color fading or discoloration of organic dyes, namely to increase their light fastness. The present invention is used very advantageously to increase the light fastness of the organic substrates.

In the present specification and the appended claims, the term "organic substrate" or "substrate compounds" include substances which look colored or colorless to the human eye under sunlight. They include substances having an absorption maximum in the visible region, such as fluorescent whitening agents, and substances having an absorption maximum in the infrared region. In the present invention, the organic substrates include organic substances having an absorption maximum at about 300 nm in the ultraviolet region to about 800 nm in the infrared region.

In the present specification and the appended claims, the terms "color" or "dye" include organic substances which appear colored to the human eye under sunlight. In the present specification and the appended claims, the term "light" denotes electromagnetic radiation having a wavelength of less than about 800 nm and includes ultraviolet rays having a wavelength of less than about 400 nm, visible rays having a wavelength of about 400 nm to about 700 nm, and infrared rays having a wavelength of about 700 to about 800 nm.

The present invention is particularly directed to improving the light fastness of organic substrate materials occurring in photographic materials, e.g., color films, prints, etc., in colored polymers useful as agricultural vinyl cover sheets, umbrellas, tents, etc.; of fluorescent whitening agents; and dyed textiles, etc.

It has been known that organic substrates, such as colors or dyes, tend to fade in color or discolor under light. Many reports have disclosed methods of reducing color fading or discoloration, and increasing light fastness. For example, U.S. Pat. No. 3,432,300 discloses that the light fastness of organic compounds such as indophenol, indoaniline, azo and azomethine dyes to visible and ultraviolet light can be improved by mixing them with phenolic compounds having a fused heterocyclic system.

Generally, in the field of silver halide photographic materials, azomethine dyes or indoaniline dyes are formed by the reaction of the oxidation product of an aromatic primary amine developing agent with a coupler, as described in Chapter 17 of C. E. K. Mees and T. H. James, "The Theory of the Photographic Process" (published in 1967 by Macmillan). A number of methods are known for improving the stability to light of images formed from these dyes, i.e. color images. For example, it is known to use hydroquinone derivatives described, for example, in U.S. Pat. Nos. 2,360,290, 2,418,613, 2,675,314, 2,701,197, 2,704,713, 2,728,659, 2,732,300, 2,735,765, 2,710,801 and 2,816,028 and British Pat. No. 1,363,921, gallic acid derivatives described, for example, in U.S. Pat. Nos. 3,457,079 and 3,069,262 and Japanese Patent Publication No. 13496/68; p-alkoxyphenols described, for example, in U.S. Pat. Nos. 2,735,765 and 3,698,909; and coumarone or coumarane derivatives described, for example, in U.S. Pat Nos. 3,432,300, 3,573,050, 3,574,627, 3,764,337, 3,574,626, 3,698,909 and 4,015,990. These compounds have an effect of inhibiting the color fading or discoloration of color images, but the effect is still insufficient.

A method for improving the stability of an organic substrate compound to light by using an azomethine quenching compound having an absorption maximum more bathochromic than the absorption maximum of the substrate compound is disclosed in British Pat. No. 1,451,000. The method, however, is disadvantageous because the azomethine quenching compound itself is strongly colored, and greatly affects the color of the substrate compound.

The use of a metal complex for prevention of the photodegradation of polymer is described by J. P. Guillory and R. S. Becker in *J. Polym. Sci.*, Polym. Chem. Ed., 12, 993 (1974), and by R. P. R. Ranaweera and G. Scott in *J. Polym. Sci.*, Polym. Lett. Ed., 13, 71 (1975). Furthermore, a method for stabilizing dyes by metal complexes is described in Japanese Patent Publication No. 87649/75 and Research Disclosure 15162 (1976). However, these complexes do not have very great discoloration preventing effects and their solubility in organic solvents is low. It is therefore impossible to add them in amounts high enough to produce a sufficient fade inhibiting effect. These complexes also suffer the defect that because they are strongly colored, they will cause deleterious effects on the color purity of the organic substrate substances, especially dyes, when they are added in large amounts.

SUMMARY OF THE INVENTION

It is therefore an object of this invention to provide a method for improving the stability of organic substrate substances to light.

Another object of this invention is to provide a method for improving the stability of organic substrates, especially colors or dyes, to light without damaging their hues and purities.

Still another object of this invention is to provide a method for improving the stability of organic substrates to light using stabilizers having a high solubility in organic solvents and high miscibility with the organic substrates.

Yet another object of this invention is to provide a method for improving the stability to light of colored images for forming color photographic images.

A further object of this invention is to provide a method for improving the stability to light of dyes formed by the reaction of aromatic primary amine developing agents with color couplers.

Other objects of this invention will become apparent from the following description.

The above and other objects of this invention are achieved by causing an organic substrate material having an absorption maximum at about 300 nm to about 800 nm to be coexistant with at least one complex of the following general formula

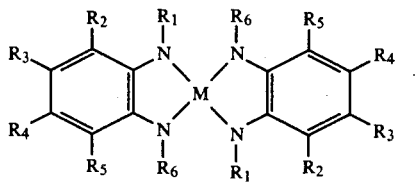

(I)

wherein M represents Cu, Co, Ni, Pd or Pt; $R_1$ and $R_6$ may be the same or different and represent a hydrogen atom or an alkyl group, an aryl group, an acyl group, an alkoxycarbonyl group, an aryloxycarbonyl group, an alkylsulfonyl group or an arylsulfonyl group; and $R_2$, $R_3$, $R_4$ and $R_5$ which may be the same or different represent a hydrogen atom, a halogen atom, a cyano group, or an alkyl group, an aryl group, a cycloalkyl group or a heterocyclic group bonded to a carbon atom on a benzene ring directly or through a divalent linking group, or $R_2$ and $R_3$, $R_3$ and $R_4$ or $R_4$ and $R_5$ respectively may combine and represent the non-metallic atomic groupings required to form a 6-membered ring.

The terms "in the presence of" or "coexistant with" as used in the specification refer not only to co-existence of the substrate material and the compound of the formula (I) in the same solution, dispersion, emulsion or layer but also to the existence of the organic substrate and the complex in adjacent layers of a multi-layered photographic material. As long as the complex compound is associated with the organic substrate material such that it improves the light fastness of the organic substrate, it is used "in the presence of" or "coexists" with the substrate for purposes of the present invention.

The alkyl group represented by $R_1$ and $R_6$ include substituted and unsubstituted alkyl groups which are either of straight or branched chain. These alkyl groups preferably contain 1 to 20 carbon atoms excluding the carbon atoms in any substituent. Examples are methyl, ethyl, propyl, butyl, hexyl, octyl, decyl, dodecyl, tetradecyl, hexadecyl, heptadecyl, and octadecyl groups.

The aryl group represented by $R_1$ and $R_6$ includes both substituted and unsubstituted monocyclic and bicyclic aryl groups preferably containing 6 to 14 carbon atoms excluding the carbon atoms in any substituent. Examples are phenyl, toluyl and naphthyl groups.

The acyl group represented by $R_1$ and $R_6$ includes both substituted and unsubstituted acyl groups preferably containing 2 to 21 carbon atoms excluding the carbon atoms in any substituent. Examples are acetyl, valeryl, stearoyl, benzoyl and naphthoyl groups.

The alkoxycarbonyl group represented by $R_1$ and $R_6$ include both substituted and unsubstituted alkoxycarbonyl groups preferably straight or branched chain containing 2 to 21 carbon atoms excluding the carbon atoms in any substituent. Examples are methoxycarbonyl, butoxycarbonyl and propoxycarbonyl groups.

The aryloxycarbonyl group represented by $R_1$ and $R_6$ includes both substituted and unsubstituted monocyclic and bicyclic aryloxycarbonyl groups preferably containing 7 to 15 carbon atoms excluding the carbon atoms in any substituent. Examples are phenoxycarbonyl and tolyloxycarbonyl groups.

The alkylsulfonyl group represented by $R_1$ and $R_6$ includes both substituted and unsubstituted alkylsulfonyl groups preferably straight or branched chain and containing 1 to 20 carbon atoms excluding the carbon atoms in any substituent. Examples are mesyl and butanesulfonyl groups.

The arylsulfonyl group represented by $R_1$ and $R_6$ includes both substituted and unsubstituted monocyclic or bicyclic aryl groups preferably monocyclic having 6 to 14 carbon atoms excluding the carbon atoms in any substituent. Examples are benzenesulfonyl and tosyl groups.

The halogen atom represented by $R_2$, $R_3$, $R_4$ and $R_5$ includes fluorine, chlorine, bromine and iodine atoms.

The alkyl group represented by $R_2$, $R_3$, $R_4$ and $R_5$ includes substituted and unsubstituted straight chain or branched chain alkyl groups preferably containing 1 to 19 carbon atoms. Examples of the straight-chain or branched-chain alkyl group represented by $R_2$, $R_3$, $R_4$ and $R_5$ are methyl, ethyl, propyl, butyl, hexyl, octyl, decyl, dodecyl, tetradecyl, hexadecyl and octadecyl groups.

The aryl group represented by $R_2$, $R_3$, $R_4$ and $R_5$ includes substituted and unsubstituted aryl groups preferably containing 6 to 14 carbon atoms. Examples of the aryl group represented by $R_2$, $R_3$, $R_4$ and $R_5$ are phenyl and naphthyl groups.

The heterocyclic group represented by $R_2$, $R_3$, $R_4$ and $R_5$ includes substituted and unsubstituted heterocyclic groups which are preferably 5- or 6-membered. The heterocyclic group represented by $R_2$, $R_3$, $R_4$ and $R_5$ is a 5- or 6-membered heterocyclic group containing at least one nitrogen, oxygen or sulfur atom as a hetero atom in the ring. Nitrogen and oxygen are preferred since there is no possibility that these heteroatoms might react with silver and caused desensitization. Examples include furyl, hydrofuryl, thienyl, pyrrolyl, pyrrolydyl, pyridyl, imidazolyl, pyrazolyl, quinolyl, indolyl, oxazolyl and thiazolyl groups.

The cycloalkyl group represented by $R_2$, $R_3$, $R_4$ and $R_5$ includes substituted and unsubstituted cycloalkyl groups which are preferably 5- or 6-membered. Examples of the cycloalkyl group represented by $R_2$, $R_3$, $R_4$ and $R_5$ are cyclopentyl, cyclohexyl, cyclohexenyl and cyclohexadienyl groups.

The six-membered ring formed by the combination of $R_2$ and $R_3$, or $R_3$ and $R_4$, or $R_4$ and $R_5$ may be an aryl group, preferably a benzene ring which may be condensed with a heterocyclic ring, such as a furan ring. The benzene ring may be substituted, unsubstituted, or fused with another aromatic ring.

Examples of the 6-membered nucleus formed by the combination of $R_2$ with $R_3$, $R_3$ with $R_4$, or $R_4$ with $R_5$ include benzene, naphthalene, isobenzothiophene, isobenzofuran and isoindoline rings.

The alkyl, cycloalkyl, aryl or heterocyclic group represented by $R_2$, $R_3$, $R_4$ and $R_5$ may be bonded to a carbon atom on a benzene ring through a divalent linking group such as an oxy group (—O—), a thio group (—S—), an amino group, an oxycarbonyl group, a carbonyl group, a carbonyloxy group, a carbamoyl group, a sulfamoyl group, a carbonylamino group, a sulfonylamino group or a sulfonyl group. Of these divalent linking groups, the groups other than sulfur are more preferred since there is no possibility that these groups might interact with the silver which sometimes causes desensitization.

Examples of the alkyl group represented by $R_2$, $R_3$, $R_4$ and $R_5$ bonded to a carbon atom in a benzene ring of the compound of formula (I) through the divalent linking group are alkoxy groups (e.g., a methoxy, ethoxy, butoxy, propoxy, n-decyloxy, n-dodecyloxy or an n- hexadecyloxy group), alkoxycarbonyl groups (e.g., a methoxycarbonyl, ethoxycarbonyl, butoxycarbonyl, n-decyloxycarbonyl or an n-hexadecyloxycarbonyl group), acyl groups (e.g., an acetyl, valeryl, stearoyl, benzoyl or a toluoyl group), acyloxy group (e.g., an acetoxy or a lauroyl group), alkylamino groups (e.g., a n-butylamino, N,N-diethylamino or a N,N-didecylamino group), alkylcarbamoyl groups (e.g., a butylcarbamoyl, N,N-diethylcarbamoyl or an n-dodecylcarbamoyl group), alkylsulfamoyl groups (e.g., a butylsulfamoyl, N,N-diethylsulfamoyl or, an n-dodecylsulfamoyl group), sulfonylamino groups (e.g., a methylsulfonylamino or a butylsulfonylamino group), sulfonyl groups (e.g., a mesyl or an ethanesulfonyl group), and acylamino groups (e.g., an acetylamino, valerylamino, palmitoylamino, benzoylamino or toluoylamino group).

Examples of the cycloalkyl group represented by $R_2$, $R_3$, $R_4$ and $R_5$ bonded to a carbon atom on a benzene ring of the compound of the invention through the divalent linking group are cyclohexyloxy, cyclohexylcarbonyl, cyclohexyloxycarbonyl, cyclohexylamino, cyclohexenylcarbonyl and cyclohexenyloxy groups.

Examples of the aryl group represented by $R_2$, $R_3$, $R_4$ and $R_5$ bonded to a carbon atom on a benzene ring of the compound of this invention through the divalent linking group are aryloxy groups (e.g., a phenoxy or naphthoxy group), aryloxycarbonyl groups (e.g., a phenoxycarbonyl or naphthoxycarbonyl group), acyl groups (e.g., a benzoyl or naphthoyl group), anilino groups (e.g., a phenylamino, N-methylanilino, or N-acetylanilino group), arylcarbamoyl groups (e.g., a phenylcarbamoyl group), arylsulfamoyl groups (e.g., a phenylsulfamoyl group), arylsulfonylamino groups (e.g., a phenylsulfonylamino or p-tolylsulfonylamino group), arylsulfonyl groups (e.g., a benzenesulfonyl or tosyl group), and acylamino groups (e.g., a benzoylamino group).

Substituents for the alkyl, aryl, cycloalkyl or heterocyclic group represented by $R_2$, $R_3$, $R_4$ and $R_5$ or the six-membered ring formed by $R_2$ and $R_3$ or, $R_3$ and $R_4$ or $R_4$ and $R_5$ include, for example a halogen atom (e.g., a chlorine, bromine or fluorine atom), a cyano group, a straight or branched chain alkyl group (e.g., a methyl, ethyl, propyl, butyl, hexyl, octyl, decyl, dodecyl, tetradecyl, hexadecyl, heptadecyl, octadecyl or methoxyethoxyethyl group), an aryl group (e.g., a phenyl, tolyl, naphthyl, chlorophenyl, methoxyphenyl or acetylphenyl group), an alkoxy group (e.g., a methoxy, ethoxy, butoxy, propoxy or methoxyethoxy group), an aryloxy group (e.g., a phenoxy, tolyloxy, naphthoxy or methoxyphenoxy group), an alkoxycarbonyl group (e.g., a methoxycarbonyl, butoxycarbonyl or phenoxymethoxycarbonyl group), an aryloxycarbonyl group (e.g., a phenoxycarbonyl, tolyloxycarbonyl or methoxyphenoxycarbonyl group), an acyl group (e.g., a formyl, acetyl, valeryl, stearoyl, benzoyl, toluoyl, naphthoyl or p-methoxybenzoyl group), an acyloxy group (e.g., an acetoxy or benzoyl group), an acylamino group (e.g., an acetamide, benzamide, or methoxyacetamide group), an anilino group (e.g., a phenylamino, N-methylanilino, N-phenylanilino or N-acetylanilino group), an alkylamino group (e.g., a n-butylamino, N,N-diethylamino or 4-methoxy-n-butylamino group), a carbamoyl group (e.g., a n-butylcarbamoyl or N,N-diethylcarbamoyl group), a sulfamoyl group (e.g., a n-butylsulfamyol, N,N-diethylsulfamoyl, n-dodecylsulfamoyl or N-(4-methoxy-n-butyl)sulfamoyl group), a sulfonylamino group (e.g., a methylsulfonylamino, phenylsulfonylamino, or methoxymethylsulfonylamino group), or a sulfonyl group (e.g., a mesyl, tosyl or methoxymethanesulfonyl group). In the above substituents the alkyl moieties are straight or branched chain and contain 1 to 20 carbon atoms and the aryl moieties are monocyclic or bicyclic and contain 6 to 14 carbon atoms.

Of the complexes represented by general formula (I), those of formula (Ia) below are preferred.

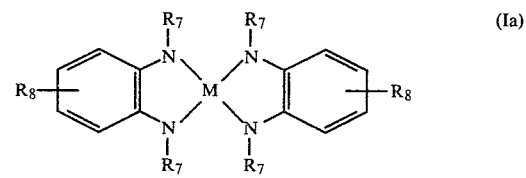

In formula (Ia), M represents the same metal atoms as defined in general formula (I); $R_7$ has the same definition as $R_1$ and $R_6$ in general formula (I); and $R_8$ has the same definition as regard to $R_2$, $R_3$, $R_4$ or $R_5$ in general formula (I) and can be connected directly to the benzene ring or through a divalent connecting group.

Examples of the complexes of general formula (I) are listed below. These examples are provided to illustrate compounds effective in the present invention and in no way is the invention limited to these illustrated compounds.

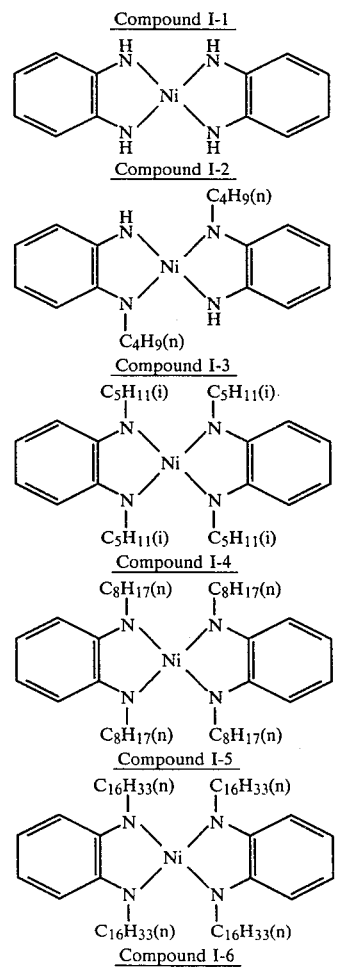

-continued
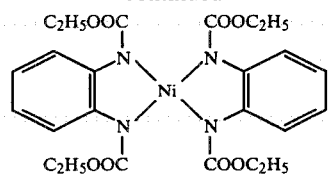
Compound I-7
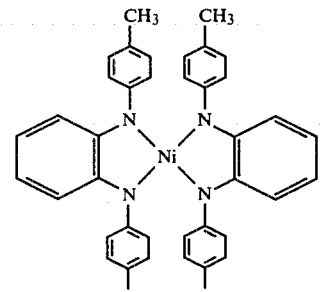
Compound I-8
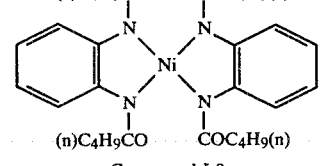
Compound I-9
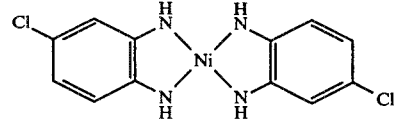
Compound I-10
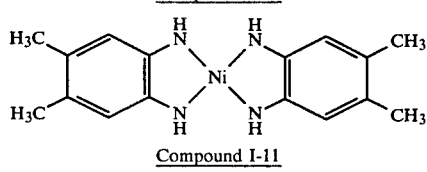
Compound I-11
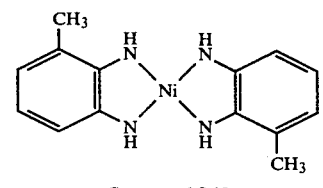
Compound I-12
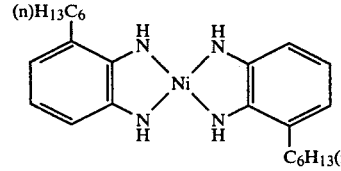
Compound I-13
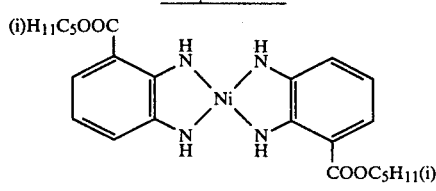
Compound I-14
-continued
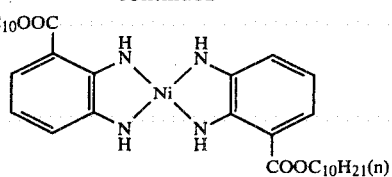
Compound I-15
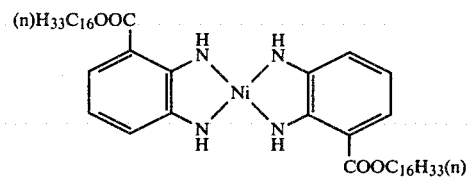
Compound I-16
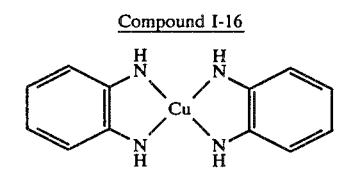
Compound I-17
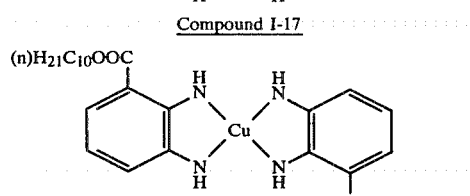
Compound I-18
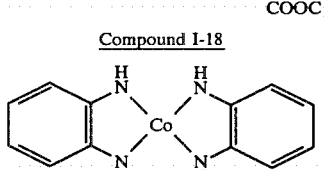
Compound I-19
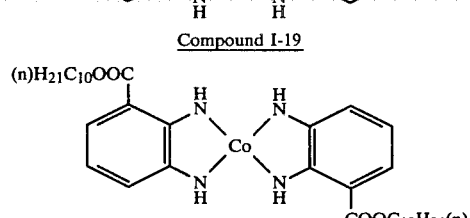
Compound I-20
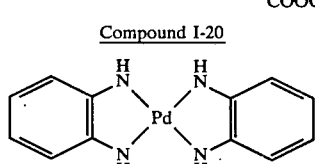
Compound I-21
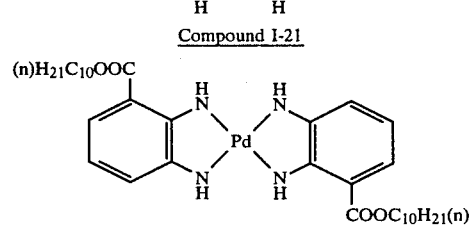
Compound I-22
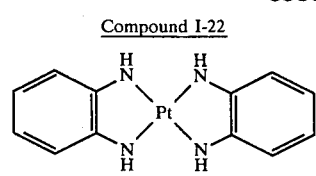
Compound I-23

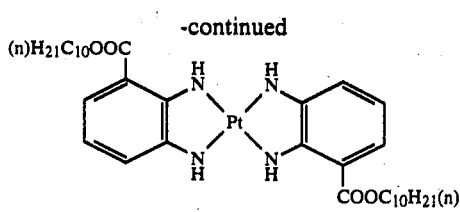

A general method of synthesis of the aforesaid complexes is described, for example, in A. L. Balch, R. H. Holm, JACS 88, 5201 (1966). An aqueous solution of a metal chloride (e.g., $NiCl_2 \cdot 6H_2O$) in conc. ammonia water is added to a solution of an equimolar amount of o-phenylenediamine derivative in water or a water-ethanol solvent mixture. The mixture is stirred at room temperature for 24 hrs. while stirring. The precipitated crystals are filtered, washed with water and dried in a conventional manner. If necessary, the crystals are recrystallized from dimethylformamidoether. Some examples are given below.

SYNTHESIS EXAMPLE 1

Synthesis of Compound I-1

Nickel chloride hexahydrate (20 g) was dissolved in 50 ml of water, and 60 ml of concentrated ammonia solution was added. An aqueous solution of 12 g of o-phenylenediamine in 1.5 liters of warm water was added to the resulting solution, and the mixture was stirred for 24 hours at room temperature. The resulting dark blue precipitate was filtered, washed with methanol, and dried under reduced pressure. 10 g product was recrystallized from a mixture of dimethyl formamide and diethyl ether.

SYNTHESIS EXAMPLE 2

Synthesis of Compound I-9

Nickel chloride hexahydrate (10 g) was dissolved in 30 ml of water, and 30 ml of concentrated ammonium solution was added. 600 ml of warm water and a solution of 8 g of 1-chloro-3,4-diaminobenzene in 200 ml of ethanol were added to the resulting solution, and the mixture was stirred at room temperature for 24 hours. The resulting dark blue precipitate was filtered, washed with methanol, and dried under reduced pressure. 8 g product was recrystallized from a mixture of dimethyl formamide and diethyl ether.

As will become apparent from the disscussion and numerous examples of the organic substrate material which follows, the present invention is applicable to a wide variety of organic materials, the essential point being that the substrates have their absorption maximum in the range of 300 to 800 nm.

The organic substrate treated in accordance with this invention include all dyes which fall into the following classification made according to dyeing characteristics, for example water-soluble dyes such as basic dyes, acid dyes, direct dyes, soluble vat dyes and mordant dyes; water insoluble dyes such as sulfide dyes, vat dyes, oil-soluble dyes, disperse dyes, azoic dyes and oxidized dyes; and reactive dyes. These organic substrate substances include not only dyes which look colored under sunlight, but also fluorescent bleaching dyes which are colorless or pale yellow under sunlight.

These dyes include all dyes which fall into the classification made according to chemical structure such as quinoneimine dyes (azine dyes, oxazine dyes, thiazine dyes, etc.), methine and polymethine dyes, (cyanine dyes, azomethine dyes, etc.), azo dyes, anthraquinone dyes, indoamine dyes, indophenol dyes, indigoid dyes, carbonium dyes, and formazan dyes.

The organic substrate substances used in this invention include image-forming dyes used in the field of photography, for example dyes formed from color couplers, DRR compounds, DDR couplers, amidolazone compounds and color developers, and dyes used in silver dye bleaching processes.

Preferred dyes for use as the organic substrate in this invention are anthraquinone, quinoneimine, azo, methine, polymethine, indoamine, indophenol and formazan dyes. Methine, polymethine, indoamine and indophenol dyes are most preferably used in the practice of this invention. The methine, polymethine, indoamine, and indophenol dyes preferably include the group of the formula

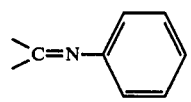

in which the phenyl group is unsubstituted, or substituted by alkyl, alkoxy, halogen, amino, etc.

The dye-forming couplers suitable for use in this invention include yellow, magenta and cyan dye-forming types. These couplers may be of the two equivalent or four equivalent type described, for example, in U.S. Pat. Nos. 3,277, 155 and 3,458,315.

Yellow dye-forming couplers generally contain a methylene group activated by at least one carbonyl group (such as an openchain ketomethylene group), and include β-diketones and β-ketoacylamides such as benzoyl acetanilide and α-pivalyl acetanilide. Suitable couplers are described, for example, in U.S. Pat. Nos. 2,428,054, 2,499,966, 2,453,661, 2,778,658, 2,908,573, 3,227,550, 3,253,924, 3,277,155 and 3,384,657, and British Patent 503,752.

Magenta dye-forming couplers such as 5-pyrazolone-type couplers can be used in this invention: Couplers of this type are described, for example, in U.S. Pat. Nos. 2,600,788, 2,725,292, 2,908,573, 3,006,759, 3,252,924, 4,026,706 and 3,311,476.

Examples of other magenta dye-forming couplers are indazolones of the type described by Vittum and Weissberger in "Journal of Photographic Science", 6, 158 (1958), pyrazolinobenzimidazole described in U.S. Pat. No. 3,061,432, pyrazolo-s-triazole described in Belgian Patent No. 724,427, and 2-cyanoacetylcoumarone described in U.S. Pat. No. 2,115,394.

The cyan dye-forming couplers that can be used in this invention include phenol and naphthol compounds. Compounds of this type are described in U.S. Pat. Nos. 2,275,292, 2,423,730, 2,474,293, 2,895,826, 2,908,573, 3,043,892, 3,227,550, 3,253,294, and 4,026,706.

Such couplers are generally described, for example, in Kirk-Othmer, "Encyclopedia of Chemical Technology", Vol. 5, pp. 822–825, and Glafkides, "Photographic Chemistry", Vol. 2, pp. 596–614.

When these couplers are used in the practice of this invention, they react with oxidized aromatic primary amine developing agents to form dyes.

The above developing agents include aminophenol and phenylenediamine, and they can be used either singly or as a mixture.

Examples of developing agents which can be reacted with couplers to form the organic substrate substances are as follows:

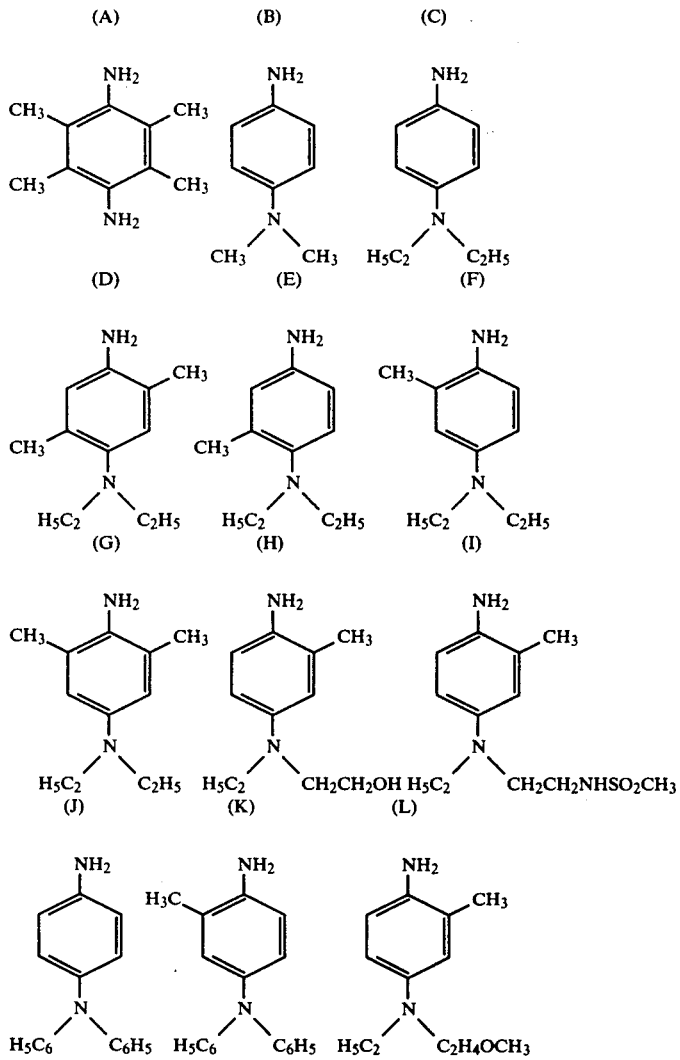

The developing agents illustrated above and others can provide organic substrates upon the reaction with photographic color couplers. Cyan, Magenta and Yellow Couplers which are preferably employed are represented by the formulae (IIa), (IIb) or (IIc) below respectively:

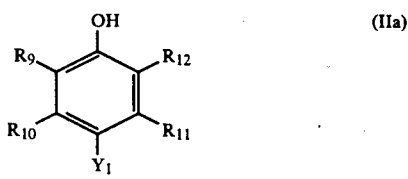

wherein $R_9$, $R_{10}$, $R_{11}$ and $R_{12}$ each represents a hydrogen atom, a halogen atom (e.g., fluorine, chlorine, bromine or iodine), an alkyl group having 1 to 20 carbon atoms (hereafter, all of the alkyl groups referred to with respect of formulae (IIa), (IIb) and (IIc) may possess 1 to 20 carbon atoms) (e.g., methyl, ethyl, octyl, dodecyl, tetradecyl, octadecyl, etc.); an alkyl- or aryl-substituted carbamoyl wherein the aryl moiety has 6 to 10 carbon atoms, (hereafter all of the aryl groups referred to with respect to formulae (IIa), (IIb) and (IIc) may possess 6 to 10 carbon atoms) (e.g., methylcarbamoyl, ethylcarbamoyl, dodecylcarbamoyl, tetradecycarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R_9$ and $R_{10}$ may combine with each other to form a sixmembered carbocyclic ring (e.g., a benzene ring which may further be substituted with an alkyl or aryl group).

$Y_1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an aminosulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R_9$, $R_{10}$, $R_{11}$ and $R_{12}$, or the 6-membered ring formed by combining $R_9$ and $R_{10}$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di(t)-amylphenoxy, etc.); a halogen atom (e.g., chlorine, bromine, fluorine, etc.); and the like.

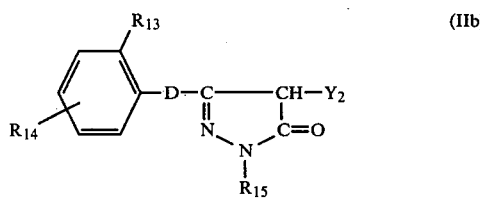
(IIb)

wherein $R_{13}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R_{12}$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc. and $R_{15}$ represents an aryl group (e.g., phenyl, naphthyl, etc.) said alkyl and aryl groups having the number of carbon atoms disscussed above with respect to formula (IIa).

D represents an amino group, a carbonylamino group, or a ureido group.

$Y_2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R_{13}$, the alkyl, amido, N-alkylcarbamoyl, N-alkylsulfamoyl, alkoxycarbonyl or acyloxy group represented by $R_{14}$, or the aryl group represented by $R_{15}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

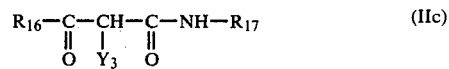
(IIc)

wherein $R_{16}$ represents an alkyl group (e.g., methyl, ethyl, (t)-butyl, (t)-octyl, etc.) or an aryl group (e.g., phenyl) and $R_{17}$ represents an aryl group (e.g., phenyl).

$Y_3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R_{16}$ and the aryl group represented by $R_{17}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc.

Examples of dyes, and couplers capable of reacting with the aforesaid or other developing agents to form substrate compounds are given below.

C-1
C-2

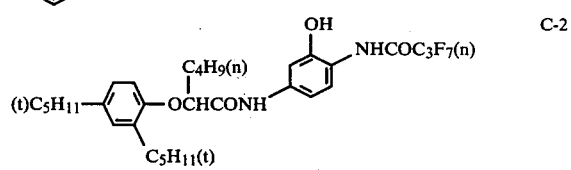
C-3

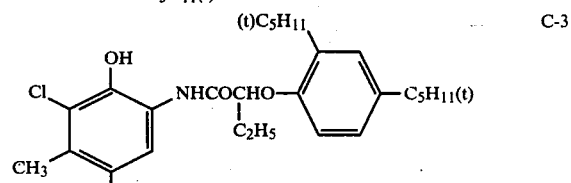
C-4

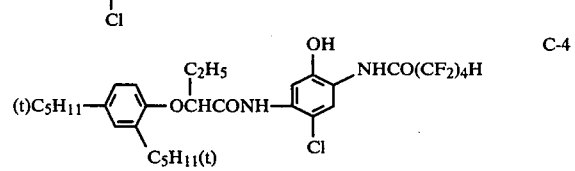
C-5

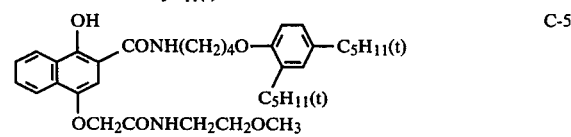

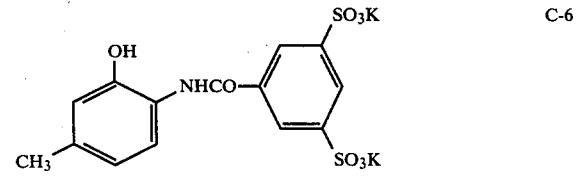
C-6

-continued
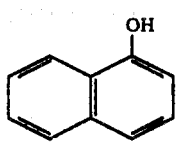
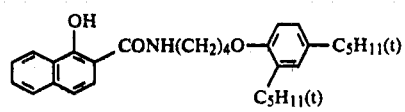
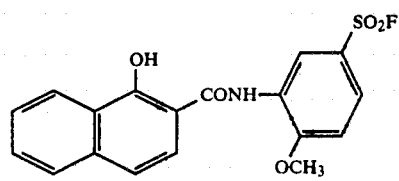
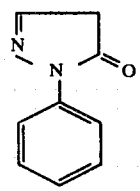
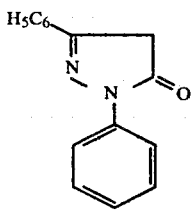
C-12
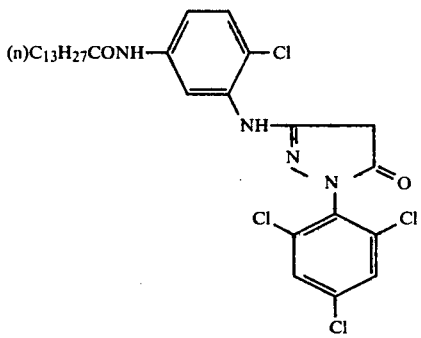
C-13
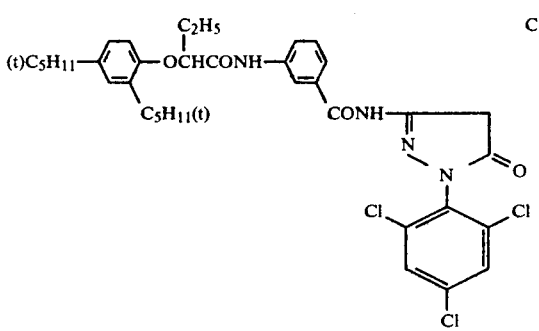
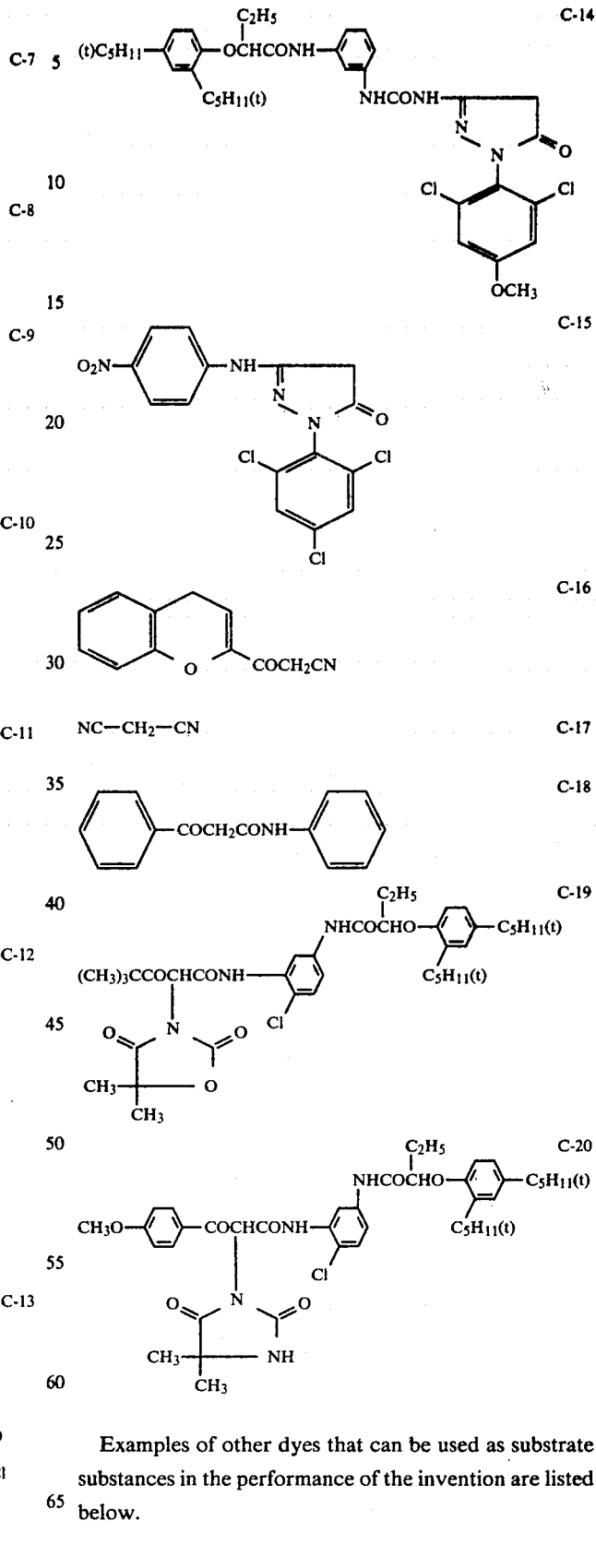
Examples of other dyes that can be used as substrate substances in the performance of the invention are listed below.

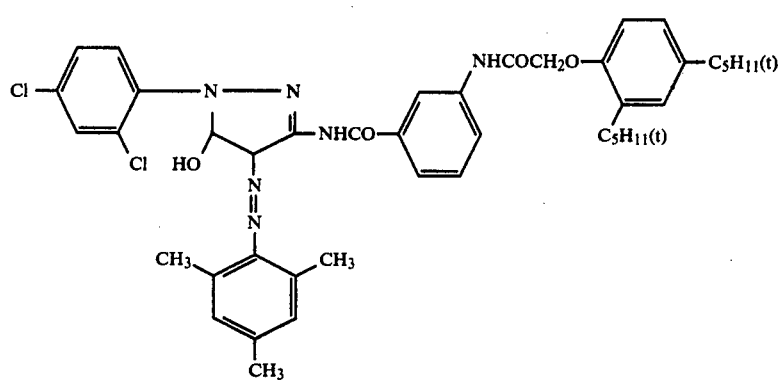
C-21
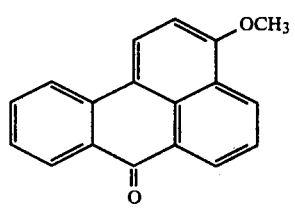
C-22
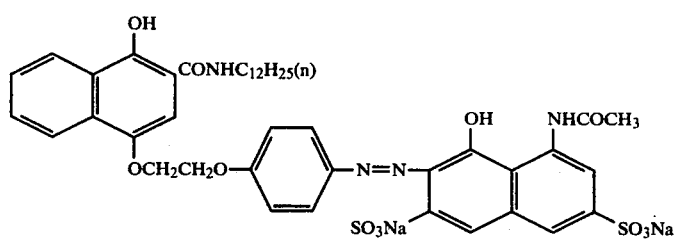
C-23
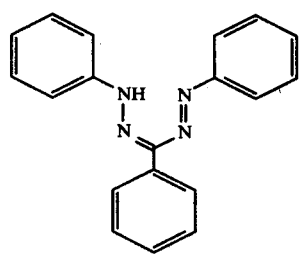
C-24
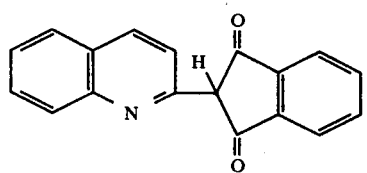
C-25
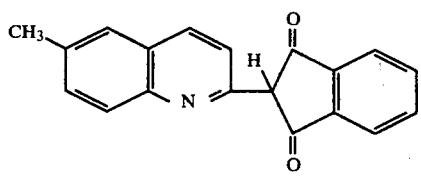
C-26

-continued
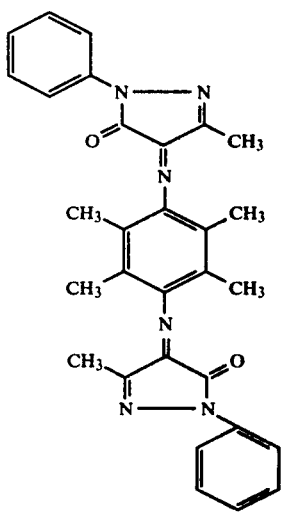
C-27
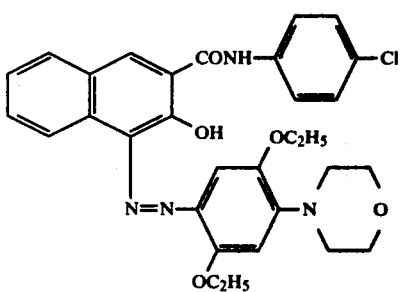
C-28
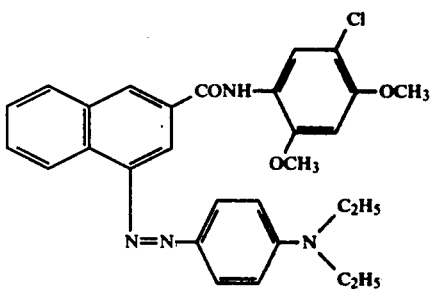
C-29
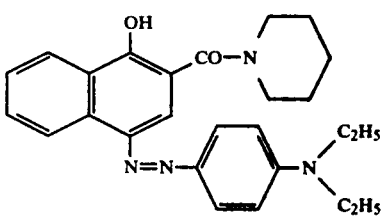
C-30
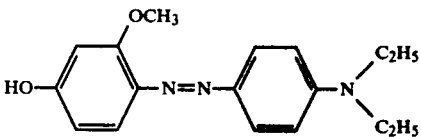
C-31
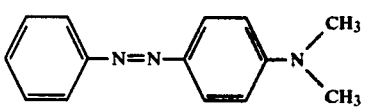
C-32

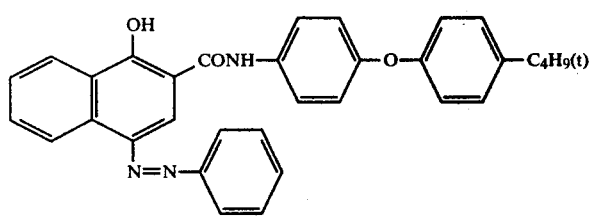 C-33
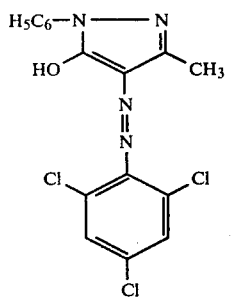 C-34
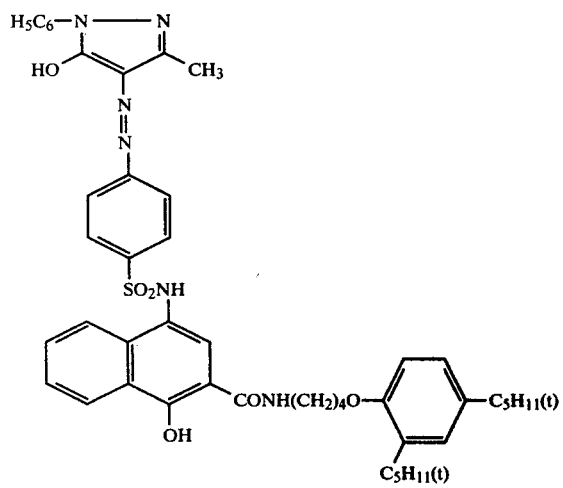 C-35
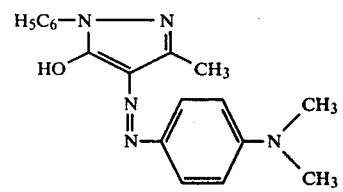 C-36
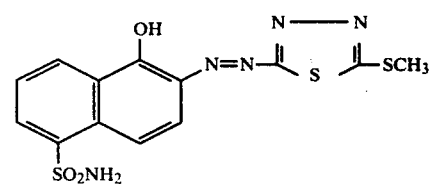 C-37
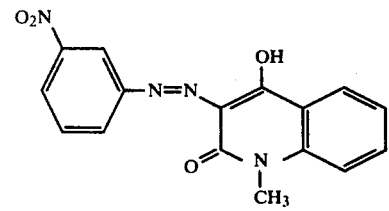 C-38

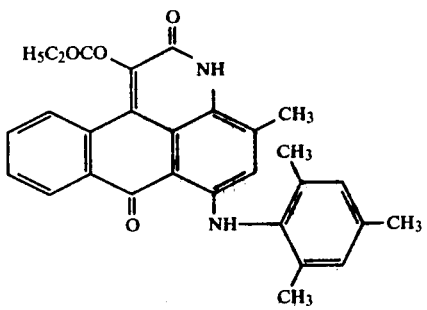
C-39
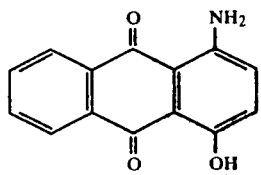
C-40
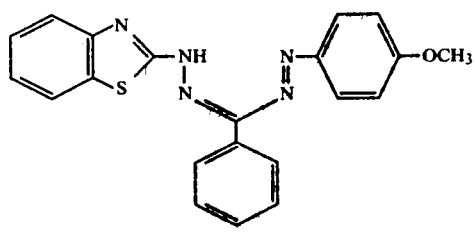
C-41
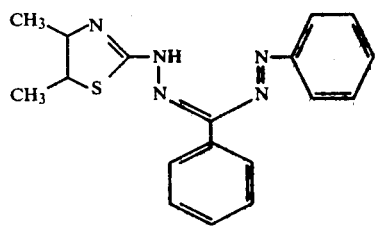
C-42
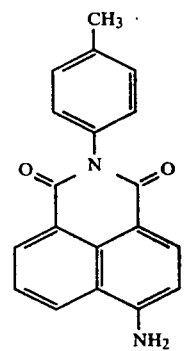
C-43
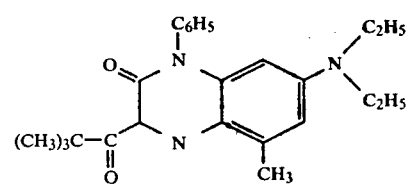
C-44
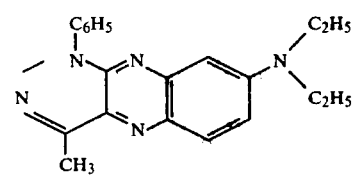
C-45

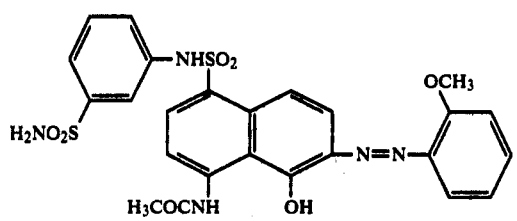
C-46
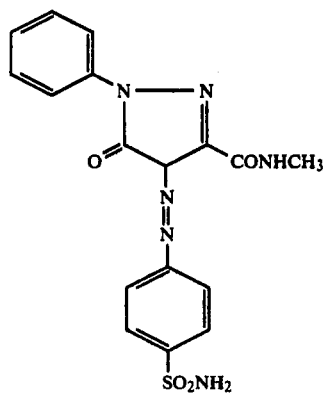
C-47
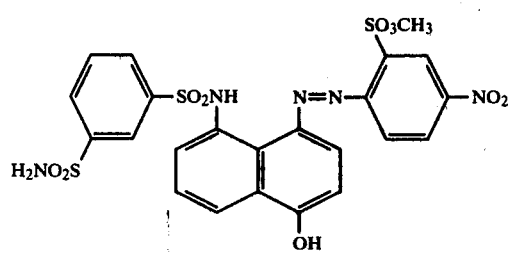
C-48
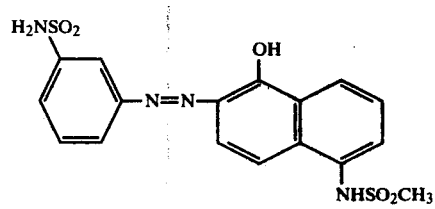
C-49
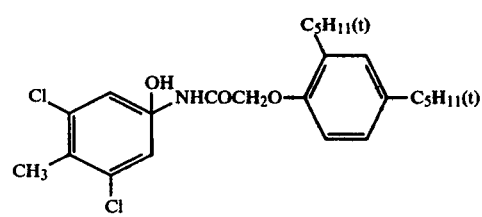
C-50
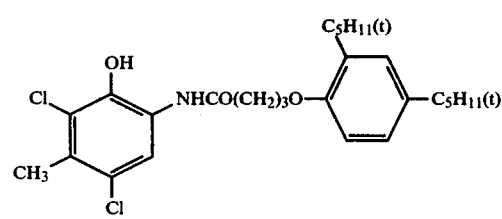
C-51
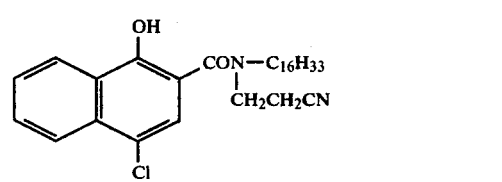
C-52

-continued
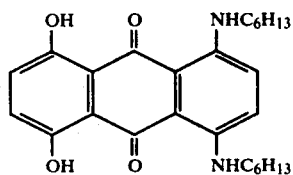 C-53
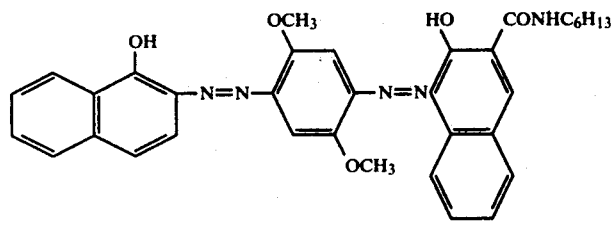 C-54
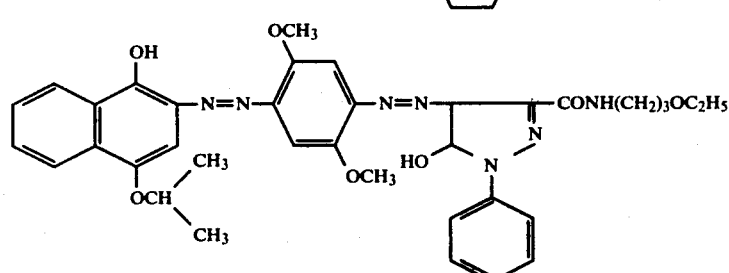 C-55
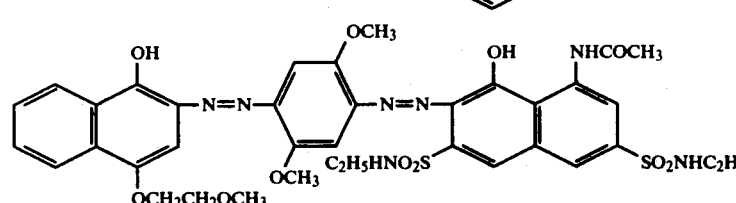 C-56
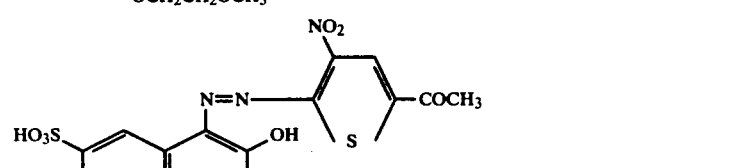 C-57
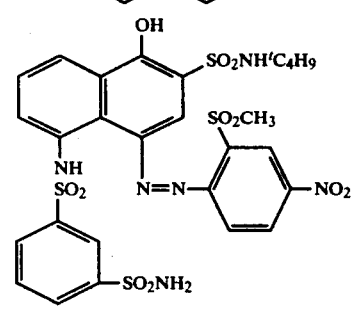 C-58
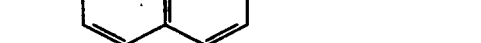 C-59
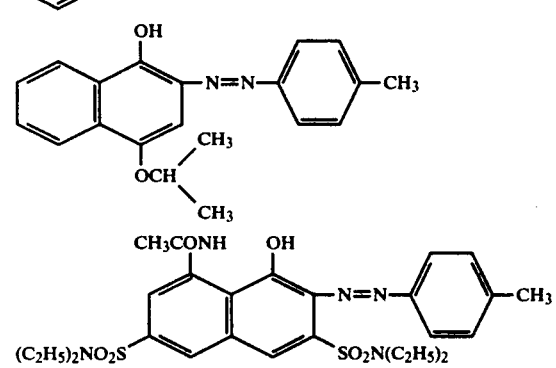 C-60

-continued
C-61
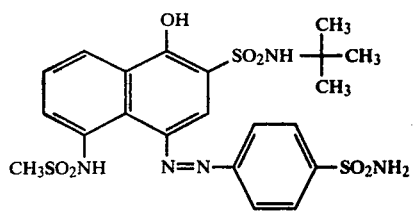
C-62
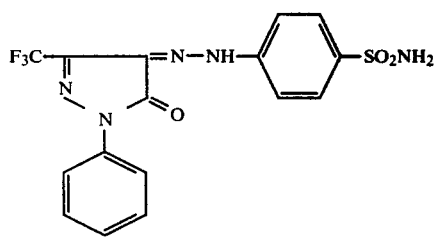
C-63
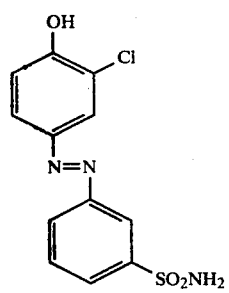
C-64
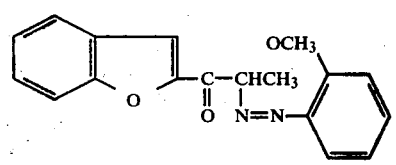
C-65
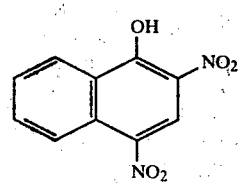
C-66
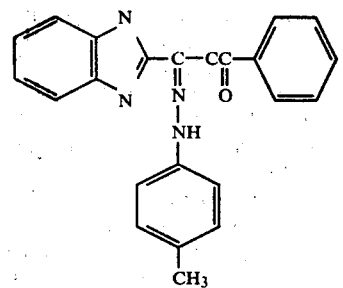
C-67
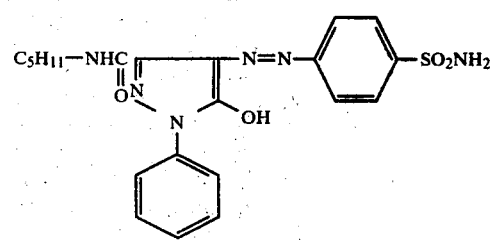

-continued

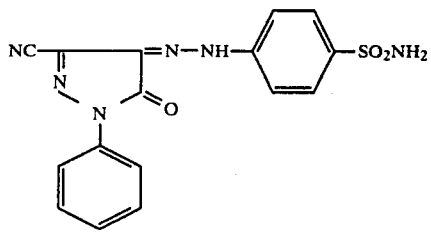
C-68

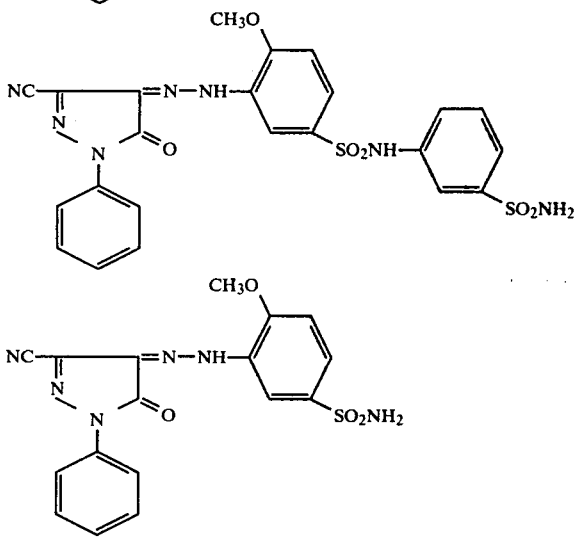
C-69

C-70

Examples of another type of dye that can be preferably used in this invention are dyes formed by the oxidation of DRR compounds described, for example, in U.S.B 351,673, U.S. Pat. Nos. 3,932,381, 3,928,312, 3,931,144, 3,954,476, 3,929,760, 3,942,987, 3,932,380, 4,013,635 and 4,013,633, Japanese Patent Application (OPI) Nos. 113624/76, 109928/76, 104343/76 and 4819/77, Japanese Patent Application No. 64,533/77, corresponding to OPI 149328/78, "Research disclosure", November 1976, and ibid. No. 1 3024 ('75).

Examples of another type of dye that can be used in this invention include dyes released upon the reaction of DDR couplers and the oxidation products of color developing agents or dyes formed by the reaction of DDR couplers with the oxidation products of color developing agents, which are described, for example, in British Pat. Nos. 840,731, 904,364, 932,272, 1,014,725, 1,038,331, 1,066,352 and 1,097,064, Japanese Patent Application (OPI) No. 133021/76, U.S. Defensive Publication T 900,029, and U.S. Pat. No. 3,227,550.

Examples of another type of dye that can be preferably used in this invention are color developing agents described, for example, in Japanese Patent Publication Nos. 182/60, 18332/60, 32130/73, 43950/71, and 2618/74.

Examples of sill another type of dye that can be used in this invention are the various dues used in the silver dye bleaching process. Examples of yellow dyes that can be used for this purpose include azo dyes such as Direct Fast Yellow GC (CI 29000) and Chrysophenine (CI 24895), and benzoquinone dyes such as Indigo Golden Yellow IGK (CI 59101), Indigosol Yellow 2GB (CI 61726), Algosol Yellow GCA-CF (CI 67301), Indanthrene Yellow GF (CI 68420), Mikethrene Yellow GC (CI 67300), and Indanthrene Yellow 4GK (CI 68405), anthraquinone-type vat dyes, polynuclear soluble vat dyes, and other vat dyes. Examples of magenta dyes include azo dyes such as Sumilight Supra Rubinol B (CI 29225) and Benzo Brilliant Geranine B (CI 15080), indigoid dyes such as Indigosol Brilliant Pink IR (CI 73361), Indigosol Violet 15R (CI 59321), Indigosol Red Violet IRRL (CI 59316), Indanthrene Red Violet RPK (CI 67895) and Mikethrene Brilliant Violet BBK (CI 6335), soluble vat dyes composed of benzoquinonic or anthraquinonic heteropolycyclic compounds, and other vat dyes. Examples of cyan dyes are azoic dyes such as Direct Sky Blue 6B (CI 24410), Direct Brilliant Blue 2B (CI 22610), and Sumilight Supra Blue G (CI 34200), phthalocyanine dyes such as Sumilight Supra Turquoise Blue G (CI 74180) and Mikethrene Brilliant Blue 4G (CI 74140), Indanthrene Turquoise Blue 5G (CI 69845), Indanthrene Blue GCD (CI 73066), Indigosol 04G (CI 73046), and Anthrasol Green IB (CI 59826).

While the mechanism whereby the complex of the present invention improves light fastness is not entirely clear, it is believed that upon exposure to light the organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention thereby effectively improves the light fastness of the organic substrate.

The complex of formula (I) in accordance with this invention can be used to stabilize the substrate compound by dissolving the complex in a low-boiling organic solvent or a water-miscible organic solvent which does not adversely affect the photographic properties of the substrate, and adding the solution to a hydrophilic colloid that is used to provide the photographic layer. Such a solvent is selected, for example, from alcohols (e.g., methanol, ethanol, isopropanol, butanol, etc.) ethers (e.g., dimethyl ether, ethyl methyl ether, diethyl ether, 1-ethoxypropane, etc.), glycols (e.g., 1,2-ethanediol, 1,2-propanediol, 1,3-propanediol, etc.), ketones (e.g., acetone, ethyl methyl ketone, 3-pentanone, etc.), esters (e.g., ethyl formate, methyl acetate, ethyl acetate, etc.), and amides (e.g., formamide, acetamide, succinamide, etc.). This stabilizing step should preferably be carried out prior to coating, for example in a step of producing a silver halide photographic emulsion, a step of emusifying a coupler, or a step of preparing a photographic coating solution.

In order to introduce the complex of formula (I) into the hydrophilic colloid constituting the photographic layer, the same method as described with respect to the dispersion of couplers can be used. For example, U.S. Pat. No. 2,304,939 discloses the use of a high-boiling organic solvent for dissolving this material. Other applicable methods are disclosed in U.S. Pat. Nos. 2,801,170, 2,801,171 and 2,949,360; in these methods, low-boiling or water-soluble organic solvents are used together with high-boiling solvents.

Examples of high-boiling solvents effective for dispersing the substrate compound and the metallic complex used in this invention include di-n-butyl phthalate, benzyl phthalate, triphenyl phosphate, tri-o-cresyl phospahte, disphenyl mono-p-tert-butylphenyl phosphate, monophenyl di-p-tert-butylphenyl phosphate, diphenyl mono-o-chlorophenyl phosphate, monophenyl di-o-chlorophenyl phosphate, 2,4-di-t-amylphenol, N,N-diethyllaurylamide, and the trioctyl phosphate and trihexyl phosphate described in U.S. Pat. No. 3,676,137.

The low-boiling or water-soluble organic solvents which can be used advantageously together with such a high-boiling organic solvent are disclosed, for example, in U.S. Pat. Nos. 3,801,171, 2,801,170 and 2,949,360.

These organic solvents include (1) substantially water-insoluble low-boiling organic solvents such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride and chloroform; and (2) water-soluble organic solvents such as methylisobutyl ketone, β-ethoxyethyl acetate, β-butoxytetrahydrofurfuryl adipate, diethylene glycol monoacetate, acetomethoxy triglycol, acetonyl acetone, diacetone alcohol, ethylene glycol, diethylene glycol, dipropylene glycol, acetone, methanol, ethanol, acetonitrile, dimethyl formamide and dioxane.

In general, the complex of the formula (I) is dissolved or suspended in an appropriate solvent which is chosen, depending upon the physical properties of the complex used, from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc. together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

The substrate material and the complex each may be present in one or more of the hydrophilic colloid layers making up the photographic element (film, paper, diffusion transfer unit, etc.). It is preferred that the metal chelate complex and the organic substrate material be present (i.e., co-exist) in the same emulsion layer, of course, the effect of the present invention can also be attained when the complex and substrate are present in contiguous layers inasmuch as diffusion is allowed to occur between the layers. Where any (further) undesirable diffusion to occur, conventional mordanting techniques could be applied to the present invention. They may be present in non-light sensitive elements or layers as well, such as the dye image receiving layer used in diffusion transfer film units. In the case of image transfer units, the metal chelate complex is preferably located in a layer where dye images are finally found, i.e., in an image-receiving layer. Usually, the dye images formed in the image-receiving layer do not diffuse into any other layer(s) so that it is easy to retain the complex in the vicinity of the dye image. When the substrate substance and the complex are included in such a non light-sensitive image-recording element, they are preferably mordanted and the complex is preferably has such ligand that it is held in the mordanted layer of the receiving layer and does not diffuse from the dye to be stabilized.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Patent Nos. 757,959 and 757,960.

The complex and substrate substance used in the performance of this invention are used together with the materials described in Product Licensing Index, Vol. 92 (December 1971), No. 9232, pages 107–110 in accordance with the methods described in it. Chapters I, II, III, IV, V, VII, VIII, IX, X, XI, XII, XIII, XIV, XV, XVI, XVII, XVIII and XXIII are applicable in this regard.

Any amount of the complex will bring about some improvement in the light fastness of the organic substrate and there is no upper limit for the amount of the complex from a theoretical standpoint. Preferably, the complex is present in an amount of at least 0.1 mol% based on 1 mol of the organic substrate material, more preferably, in an amount of 0.1 to 1000 mol%, and most preferably, in an amount of 1 to 300 mol%. In the case of a photographic material, the amount is often expressed in a weight unit per square meter of photographic material which can be calculated from the parameters set out above. For convenience, however, in the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology.

As is well known to those skilled in the art, the substrate material is preferably present in the range of from about 10 to $10^3$ micromoles per square meter of the photographic material. A more preferably range is from about 100 to about $3 \times 10^3$ micromoles per square meter of the photographic product.

The substrate compounds used in the performance of the present invention generally have a maximum wavelength absorption peak at a wevelength less than about 800 nm. The maximum wavelength absorption peak of the substrate substance is preferably in the range of about 300 to about 800 nm, more preferably in the range of about 400 to about 800 nm.

Photographic materials used in practicing the process of this invention include supports commonly used in photographic materials. Examples of such supports include a cellulose nitrate film, a cellulose acetate film, a cellulose acetate butyrate film, a cellulose acetate propionate film, a polystyrene film, a polyethylene terephthalate film, a polycarbonate film, laminates of these films, and paper. Baryta paper; papers coated with a polymer of an α-olefin, especially the one containing 2 to 10 carbon atoms such as polyethylene or polypropylene; and plastic films whose surfaces are roughened to increase adhesion to other polymeric substances as shown in Japanese Patent Publication No. 19068/72 are also suitable support.

Various hydrophilic colloids may be used in the photographic materials used in the present invention. Hydrophilic colloids used as a binder for photographic silver halide emulsions and/or other colloid layers or a photographic material include, for example, gelatin, colloidal albumin, casein, carboxy methyl cellulose, hydroxyethyl cellulose, derivatives, agar, sodium alginate, sugar derivatives such as starch derivatives, and synthetic hydrophilic colloids such as polyvinyl alcohol, poly(N-vinyl pyrrolidone), an acrylic acid copolymer, a maleic anhydride copolymer, polyacrylamide, and derivatives and partially hydrolyzed products of these synthetic hydrophilic colloids. As required, a compatible mixture of two or more of these colloids is used.

Among these gelatin is most commonly used. Gelatin may be replaced partially or wholly by a synthetic polymeric material. A gelatin derivative can also be used which is obtained by treating and modifying functional groups in the molecule such as amino, imino, hydroxy or carboxyl groups with reagents having one group capable of reacting with them. There can also be used graft polymers obtained by linking the molecular chain of another polymeric material to gelatin.

The photographic emulsion layers and other layers used in this invention may contain a synthetic polymeric compound such as a latex-type aqueous dispersion of a vinyl polymer, especially a compound which increases the dimensional stability of photographic material, a mixture of different kinds of such polymer, or a mixture of it with a hydrophilic water-permeable colloid.

The silver halide photographic emulsion used in the invention is prepared usually by mixing a solution of a water-soluble silver salt (e.g., silver nitrate) and a solution of a water-soluble halogen salt (e.g., potassium bromide) in the presence of a solution of a water-soluble polymer such as gelatin. The silver halide may include not only silver chloride and silver bromide but also mixed silver halides such as silver chlorobromide, silver iodobromide, or silver chloroiodobromide. The silver halide grains are prepared by known conventional methods. A single or double jet method and a control double jet method are also useful. It is also possible to mix two or more separately prepared silver halide photographic emulsions.

Various compounds can be added to the photographic emulsion to prevent the occurrence of fog or the reduction of sensitivity during the preparation, storage or processing of the photographic material. Numerous compounds have been known from old as such inhibitor compounds; they include, for example, 4-hydroxy-6-methyl-1,3,3a,7-tetrazaindene. 3-methylbenzothiazole, 1-phenyl-5-mercaptotetrazole, other heterocyclic compounds, mercury-containing compounds, mercapto compounds, and metal salts.

The silver halide emulsion used in this invention can be chemically sensitized in a customary manner. Chemical sensitizers include, for example, gold compounds such as chloroaurates and gold trichloride, salts of noble metals such as platinum, palladium, iridium, and rhodium, sulfur compounds capable of forming silver sulfide by reaction with a silver salt (such as sodium thiosulfate), stannous acid salts, amines, and other reducing compounds.

If desired, the photographic emulsion used in this invention may be spectrally sensitized or supersensitized with one or more cyanine dyes such as cyanine, merocyanine or carbocyanine, or a combination of a cyanine dye with a styryl dye. The type of sensitization can be selected according to the purpose and use of the photographic material in accordance with the wavelength region for which sensitization is desired, the sensitivity of the photographic material required, etc.

The hydrophilic colloid layer of the photographic material used in the invention may, if desired, be cured with various curing agents. Examples of the curing agents are aldehdye compounds, active halogen compounds, vinylsulfone compounds, carbodiimide compounds, N-methylol compounds, and epoxy compounds.

In one embodiment of applying the method of this invention to color photographic material, the photographic material is exposed imagewise, and then processed in a customary manner to form a color image. The process includes color development, bleaching and fixing as main steps, and optionally, rinsing and stabilizing steps. Two or more steps may be carried out in a single bath, for example in the case of bleaching-fixing operation. Color development is carried out usually in an alkaline solution containing an aromatic primary amine developing agent. Examples of preferred aromatic primary amine developing agents are compounds of structural formulae (A) to (L) given hereinabove.

In another embodiment of applying the method of the invention to color photographic material which is a color diffusion transfer film unit, the processing of the photographic material is automatically performed within the photographic material. In this case, the developing agent is contained in a rupturable container. In addition to the compounds of formulae (A) to (L), N-methylaminophenol, 1-phenyl-3-pyrazolidone, 1-phenyl-4,4-dimethyl-3-pyrazolidone, 1-phenyl-4-methyl-hydroxymethyl-5-pyrazolidone, and 3-methoxy-N,N-diethyl-p-phenylene-diamine can also be used as the developing agent.

Formation of a color image in the photographic material used in this invention can be performed by known methods such as by the coupling reaction between a color coupler of the type described hereinabove and an oxidation product of a p-phenylene-diamine tye color developing agent, by a color developing agent, by the oxidative cleavage of a DRR compound, by splitting off a dye by a coupling reaction of a DDR coupler, a method using a dye-forming reaction by a coupling reaction of a DRR coupler, or a silver dye bleaching method.

Accordingly, the method of this invention can be applied to various kinds of color photographic materials such as a color positive film, a color paper, a color negative film, a color reversal film, a color diffusion transfer film unit, or a silver dye bleaching photographic material.

The following Examples illustrate the present invention in greater detail.

EXAMPLE 1

0.1 g of 1-(2,4,6-trichlorophenyl)-3-(2-chloro-5-tetradecanamide)anilino-4-[4-(N-ethyl-N-β-methanesulfonamide-ethyl)aminophenylimino]-5-oxo-2-pyrazoline was dissolved in 3 ml of trioctyl phosphate and 5 ml of ethyl acetate. The solution was dispersed in 10 g of 10% gelatin containing 1 ml of a 1% aqueous solution of sodium dodecylbenzenesulfonate. The dispersion was then mixed with 10 g of 10% gelatin. The mixture was coated on a paper support laminated on both surfaces with polyethylene, and dried. The resulting product was designated as sample A.

Sample B was prepared by the same procedure as described above except that 20 mg of Compound (I-1) of the invention was added in the preparation of the dispersion.

Samples C and D were prepared except that 2,5-di-tert-octyl hydroquinone, a known light discoloration inhibitor for dyes, was added in an amount of 25 mg, and 250 mg, respectively.

Coating was performed so that the amount of the dye was 60 mg/m$^2$ and the amount of Compound (I-1) was 12 mg/m$^2$ and the coated amount of the octyl hydroquinone was 15 and 150 mg/m$^2$ respectively.

Each of these Samples A to D was subjected to a discoloration test for 48 hours using a xenon tester (illuminance 200,000 lux) fitted with an ultraviolet ray filter C 40 (a product of Fuji Photo Film Co., Ltd.). The results are shown in Table I.

TABLE I

| Sample | Initial Density | Density after 48 hours |
|---|---|---|
| A | 0.83 | 0.02 |
| B | 0.84 | 0.71 |
| C | 0.84 | 0.09 |
| D | 0.86 | 0.38 |

The density measurement was performed by using a Macbeth densitometer (Model RD 514) with a green filter of status AA filter.

The results demonstrate that Sample B containing the Compound (I-1) of the invention showed far less discoloration than samples A, C and D. Particularly, in spite of the fact that 2,5-di-tert-octyl hydroquinone was added to samples C and D in an amount equimolar to, or 10 molar times, the amount of the Compound (I-1) of the invention in Sample B, it was scarcely effective for the prevention of discoloration. This shows that the Compound (I-1) of the invention exhibits a surprising effect in preventing the discoloration of dyes under light.

EXAMPLE 2

0.1 g of Compound (C-23) was dissolved in 0.2 cc of 1 N sodium hydroxide and 2 cc of methanol, and the solution was added to 10 g of 10% gelatin.

The mixture was coated on a paper support with polyethylene laminated to both surfaces so that the amount of the Compound (C-23) coated became 80 mg/m$^2$. The resulting product was designated as Sample E.

The same procedure as above as followed, and immediately before coating, a solution of 70 mg of the Compound (I-10) of the invention in 2 cc of methanol was added. The resulting mixture was coated in the same way as above to provide a coated amount of Compound (I-10) of 56 mg/m$^2$. The resulting product was designated as Sample F.

For comparison, Sample G was prepared in the same way as above except that 100 mg of α-tocopherol, a known light discoloration inhibitor for dyes, was added to the coating dispersion to provide a coating amount of 80 mg/m$^2$.

Each of these samples was subjected to the same discoloration test as in Example 1 for 12 hours using an ultraviolet ray absorbing filter. The results are shown in Table II.

TABLE II

| Sample | Initial density | Density after 12 hours |
|---|---|---|
| E | 0.90 | 0.05 |
| F | 0.90 | 0.62 |
| G | 0.93 | 0.15 |

The measurement was made by using a Macbeth densitometer as in Example 1. The results in the table show that the Compound (I-10) of the invention has a very great effect in preventing discoloration under light.

EXAMPLE 3

10 g of magenta coupler 1-(2,4,6-trichlorophenyl)-3-[(2-chloro-5-tetradecanamide)anilino]-2-pyrazolin-5-one was dissolved in 30 ml of trioctyl phosphate, 5 ml of dimethyl formamide and 15 ml of ethyl acetate. The solution was dispersed in 80 g of 10% gelatin solution containing 8 ml of a 1% aqueous solution of sodium dodecylbenzenesulfonate.

The resulting dispersion was mixed with 145 g (7 g as Ag) of a green-sensitive silver chlorobromide (50 mole% Br), and sodium dodecylbenzenesulfonate was added as a coating aid. The mixture was coated on a paper support with polyethylene laminated to both surfaces so that the amount of the coupler coated was 400 mg/m$^2$. The resulting product was designated as Sample H.

The same procedure as above was repeated except that 0.4 g of the Compound (I-15) of the invention was added at the time of preparing the coating dispersion. The product was designated as Sample I and coated in an amount of 16 mg/m².

Sample J was prepared in the same manner as Sample H except that 2.5 g of 2,2'-methylene-bis(4-methyl-6-tert-butylphenol), a known light discoloration inhibitor for dyes, was added instead of the compound of the invention and coated in a coating amount of the butylphenol of 100 mg/m².

Each of these samples was exposed for 1 second at 1000 lux, and processed with the following processing solutions.

| Developer | |
|---|---|
| Benzyl alcohol | 15 ml |
| Diethylenetriamine pentaacetic acid | 5 g |
| KBr | 0.4 g |
| Na₂SO₃ | 5 g |
| Na₂CO₃ | 30 g |
| Hydroxylamine sulfate | 2 g |
| 4-Amino-3-methyl-N-ethyl-N-β-(methanesulfonamide)ethyl-aniline sesquisulfate monohydrate | 4.5 g |
| Water to make | 1,000 ml |
| pH | 10.1 |
| Bleach-fixation bath | |
| Ammonium thiosulfate (70% by weight) | 150 ml |
| Na₂SO₃ | 5 g |
| Na[Fe(EDTA)] | 40 g |
| EDTA | 4 g |
| Water to make | 1,000 ml |
| pH | 6.8 |
| Processing steps | Temperature (°C.) | Time (minutes) |
| Developer | 33 | 3.5 |
| Bleach-fixation bath | 33 | 1.5 |
| Rinsing | 28–35 | 3 |

Each of the samples having a color image formed in this manner was exposed to sunlight for 2 weeks through an ultraviolet absorption filter C-40 (a product of Fuji Photo Film Co., Ltd.) capable of cutting light having a wavelength of less than 400 mμ. The density measurement was made by using a Macbeth densitometer (Model RD-514, status AA filter), and density variations in areas having an initial density of 2.0 were determined. The results are shown in Table III.

TABLE III

| Sample | Density in area having initial density of 2.0 | % Color remaining* |
|---|---|---|
| H | 0.78 | 39 |
| I | 1.76 | 88 |
| J | 1.32 | 66 |

*% Color remaining = (density after discoloration/2.0) × 100

It is seen from the results that the Compound (I-15) of the invention is an effective discoloration inhibitor.

EXAMPLE 4

A solution of 50 mg of a dye having the structure below and 500 mg of polycarbonate Lexan 145 (tradename, manufactured by General Electric Co.) in 100 ml of dichloromethane was coated onto a glass plate using a spinner. A magenta-colored film of 5.5 μm thickness was thus prepared as Sample K.

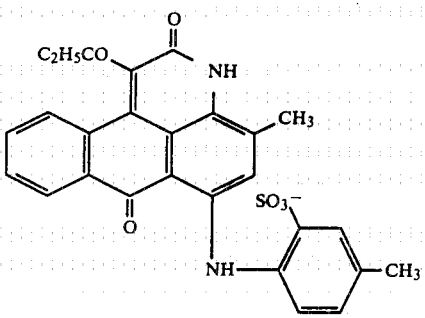

In a similar manner, five kinds of colored films were prepared as Samples L, M, N, O and P except that Compounds (I-1), (I-16), (I-18), (I-20) and (I-22) were further incorporated into the solution, respectively.

The coating rates of the dye and the fade prevention compounds were 500 mg/m² and 50 mg/m², respectively.

The thus obtained film were exposed to sunlight for one month and a color fading test was carried out.

The results obtained are shown in Table IV, in which the density was measured at 550 nm.

TABLE IV

| Sample | Initial density | Density after fading |
|---|---|---|
| K | 1.0 | 0.50 |
| L | 1.0 | 0.85 |
| M | 1.0 | 0.85 |
| N | 1.0 | 0.80 |
| O | 1.0 | 0.90 |
| P | 1.0 | 0.60 |

It can be clearly understood from the results shown in the foregoing table that the system of the instant invention, particularly Samples L and O, showed only a 10% reduction in density after the one month color fading, whereas the density of the system where no chelate complex was present was reduced 55%. That is, the system of the instant invention exhibits superior light fastness to Sample K.

Briefly summarizing the effects achieved by the metal chelate complex employed in the present invention:

(1) The metal chelate complex is readily soluble in organic solvents.
(2) In addition, the structure of the chelate complex can easily be modified so that it permits a large latitude for obtaining desired solubility.
(3) As a result of the latitude of its solubility, the complex is readily enveloped in oil droplets and as a result, photographically undesired interaction with silver halide (e.g., densentization) is avoidable.
(4) Due to its extremely high solubility, a small amount of the complex is sufficient to effect light fastness; conversely, a large amount can be employed as in the case of umbrellas, agricultural vinyl cover sheets, etc.
(5) Where the chelate is used in a photographic element, no adverse effect on photographic properties is encountered.
(6) The complex is the first fading prevention agent suitable for improving the light fastness of cyan dye images.

For the reasons above, the metal chelate complex used in the present invention provides excellent light fastness.

While the invention has been described in detail and with reference to specific embodiments thereof, it will be apparent to one skilled in the art that various changes and modifications can be made therein without departing from the spirit and scope thereof.

What we claim is:

1. A method for stabilizing photographically useful organic substrate against light, said organic substrate being selected from the group consisting of anthraquinone dyes, quinoneimine dyes, azoic dyes, methine dyes, polymethine dyes, indoamine dyes, indigoid dyes, indophenol dyes, carbonium dyes and formazan dyes, which comprises causing an organic substrate substance having an absorption maximum in the range of about 300 nm to about 800 nm to be present together with at least one complex of the formula

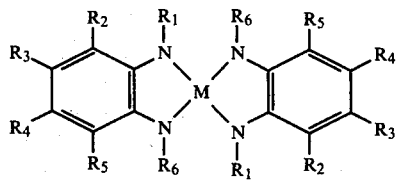

wherein M represents a Cu, Co, Ni, Pd or Pt atom, $R_1$ and $R_6$ are the same or different, and represent a hydrogen atom or an alkyl group, an aryl group, an acyl group, an alkoxycarbonyl group, an aryloxycarbonyl group, an alkylsulfonyl group, or an arylsulfonyl group; $R_2$, $R_3$, $R_4$ and $R_5$ which may be the same or different represent a hydrogen atom, a halogen atom, a cyano group, or an alkyl group, an aryl group, a cycloalkyl group or a heterocyclic group bonded to a carbon atom on the benzene rings either directly or through a divalent linking group, or $R_2$ and $R_3$, $R_3$ and $R_4$ or $R_4$ and $R_5$ may combine to form the non-metallic atomic groupings necessary to form a 6-membered ring, said compound of the formula (I) being present in a stabilizing amount which does not adversely affect color hue as well as color purity of the photographically useful organic substrate material.

2. The method of claim 1 wherein the complex is represented by the following formula

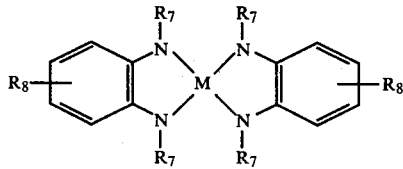

wherein $R_7$ represents a hydrogen atom or an alkyl group, an aryl group, an acyl group, an alkoxycarbonyl group, an aryloxycarbonyl group, an alkylsulfonyl group, or an arylsulfonyl group; and $R_8$ represents a hydrogen atom, a halogen atom, a cyano group, or an alkyl group, an aryl group, a cycloalkyl group, or a heterocyclic group bonded to a carbon atom on the benzene ring either directly or through a divalent linking group.

3. The method of claim 1 wherein said dye is a color photographic image formed from a dye-forming coupler, a DDR coupler, a DRR compound, a dye developer or a silver color bleaching dye.

4. The method of claim 3 wherein said dye-forming coupler is a yellow dye-forming coupler, a magenta dye-forming coupler or a cyan dye-forming coupler.

5. The method of claim 1 wherein said dye is an azomethine or indoaniline photograhic dye image.

6. A color photographic material comprising at least one layer containing a photographic dye image wherein said layer or adjacent layer contains a compound of the formula (I) in an amount sufficient to stabilize said color photographic material against the action of light while not adversely affecting color hue as well as color purity of the color photographic material

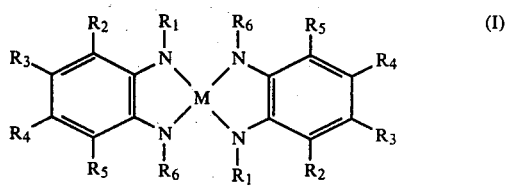

wherein M represents a Cu, Co, Ni, Pd or Pt atom; $R_1$ and $R_6$ are the same or different, and represent a hydrogen atom or an alkyl group, an aryl group, an acyl group, an alkoxycarbonyl group, an aryloxycarbonyl group, an alkylsulfonyl group, or an arylsulfonyl group; $R_2$, $R_3$, $R_4$ and $R_5$ which may be the same or different represent a hydrogen atom, a halogen atom, a cyano group, or an alkyl group, an aryl group, a cycloalkyl group or a heterocyclic group bonded to a carbon atom on the benzene rings either directly or through a divalent linking group, or $R_2$ and $R_3$, $R_3$ and $R_4$ or $R_4$ and $R_5$ may combine to form the non-metallic atomic groupings necessary to form a 6-membered ring.

7. The color photographic material of claim 6, wherein said photographic dye image is formed from a color coupler, a DDR coupler, a DRR compound, a dye developer, or as a result of a silver dye bleaching process.

8. The photographic element of claim 6, wherein said dye is formed by the reaction of a primary aromatic amine color developing agent and a cyan, magenta or yellow dye image forming coupler.

9. The photographic material of claim 6, wherein said compound is represented by the general formula (Ia)

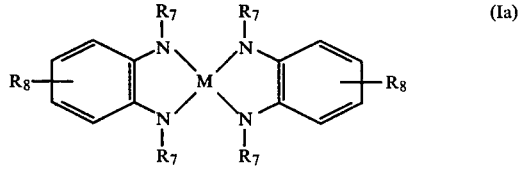

wherein $R_7$ represents a hydrogen atom or an alkyl group, an aryl group, an acyl group, an alkoxycarbonyl group, an aryloxycarbonyl group, an alkylsulfonyl group, or an arylsulfonyl group; and $R_8$ represents a hydrogen atom, a halogen atom, a cyano group, or an alkyl group, an aryl group, a cycloalkyl group, or a heterocyclic group bonded to a carbon atom on the benzene ring either directly or through a divalent linking group.

10. The photographic material of claim 6, wherein said photographic dye image is composed of a dye selected from the group consisting of anthraquinone dyes, quinoneimine dyes, azoic dyes, methine dyes, polymethine dyes, indoamine dyes, indigoid dyes, indephenol dyes, carbonium dyes and formazan dyes.

11. The photographic material of claim 6, wherein said dye-forming coupler is a yellow dye-forming coupler, a magenta dye-forming coupler or a cyan dye-forming coupler.

12. The photographic material of claim 6, wherein said dye image is composed of an azomethine or indoaniline dye.

13. A diffusion transfer color photographic material comprising a photosensitive element and an image receiving element said image receiving element comprising a support having thereon a mordanting layer containing a complex or the formula (I) in an amount sufficient to stabilize said diffusion transfer photographic material against the action of light while not adversely affecting color hue as well as color purity of the diffusion transfer color photographic material

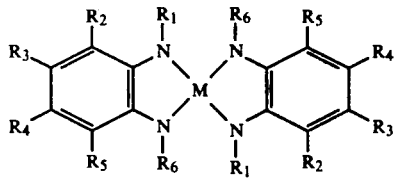

(I)

wherein M represents a Cu, Co, Ni, Pd or Pt atom; $R_1$ and $R_6$ are the same or different, and represent a hydrogen atom or an alkyl group, an aryl group, an acyl group, an alkoxycarbonyl group, an aryloxycarbonyl group, an alkylsulfonyl group, or an arylsulfonyl group; $R_2$, $R_3$, $R_4$ and $R_5$ which may be the same or different represent a hydrogen atom, a halogen atom, a cyano group, or an alkyl group, an aryl group, a cycloalkyl group or a heterocyclic group bonded to a carbon atom on the benzene rings either directly or through a divalent linking group, or $R_2$ and $R_3$, $R_3$ and $R_4$ or $R_4$ and $R_5$ may combine to form the non-metallic atomic groupings necessary to form a 6-membered ring.

14. The diffusion transfer color photographic material of claim 13 wherein said complex is of the formula (Ia)

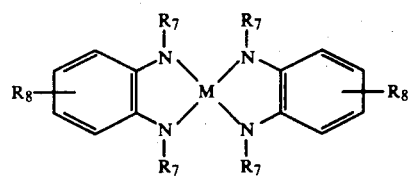

(Ia)

wherein $R_7$ represents a hydrogen atom or an alkyl group, an aryl group, an acyl group, an alkoxycarbonyl group, an aryloxycarbonyl group, an alkylsulfonyl group or an arylsulfonyl group; and $R_8$ represents a hydrogen atom, a halogen atom, a cyano group, or an alkyl group, an aryl group, a cycloalkyl group or a heterocyclic group bonded to a carbon atom on the benzene ring either directly or through a divalent linking group.

* * * * *